US008335563B2

(12) United States Patent
Stessman

(10) Patent No.: US 8,335,563 B2
(45) Date of Patent: Dec. 18, 2012

(54) MRI DETECTOR FOR IMPLANTABLE MEDICAL DEVICE

(75) Inventor: Nicholas J. Stessman, Minneapolis, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 190 days.

(21) Appl. No.: 12/409,766

(22) Filed: Mar. 24, 2009

(65) Prior Publication Data

US 2009/0182389 A1    Jul. 16, 2009

Related U.S. Application Data

(63) Continuation of application No. 11/276,159, filed on Feb. 16, 2006, now Pat. No. 7,509,167.

(51) Int. Cl.
*A61N 1/362* (2006.01)
(52) U.S. Cl. .................... 607/9; 607/10; 607/11
(58) Field of Classification Search .......... 607/2–11, 607/23–33, 59–64, 115–116
See application file for complete search history.

(56) References Cited

U.S. PATENT DOCUMENTS

| 5,287,059 | A | 2/1994 | Ando et al. |
| 5,545,187 | A | 8/1996 | Bergstrom et al. |
| 5,662,694 | A | 9/1997 | Lidman et al. |
| 7,050,855 | B2 | 5/2006 | Zeijlemaker et al. |
| 7,082,328 | B2 | 7/2006 | Funke |
| 7,242,981 | B2 | 7/2007 | Ginggen |
| 7,369,898 | B1 | 5/2008 | Kroll et al. |
| 7,509,167 | B2 | 3/2009 | Stessman |
| 7,561,915 | B1 | 7/2009 | Cooke et al. |
| 7,623,930 | B2 | 11/2009 | Zeijlemaker et al. |
| 7,672,726 | B2 | 3/2010 | Ginggen |
| 2003/0144705 | A1 | 7/2003 | Funke |
| 2004/0052392 | A1* | 3/2004 | Sacha et al. ............ 381/331 |
| 2004/0267233 | A1* | 12/2004 | Ginggen ............ 604/500 |
| 2006/0167496 | A1 | 7/2006 | Nelson et al. |
| 2006/0293591 | A1 | 12/2006 | Wahlstrand et al. |
| 2007/0191914 | A1 | 8/2007 | Stessman |
| 2011/0160565 | A1 | 6/2011 | Stubbs et al. |
| 2011/0160806 | A1 | 6/2011 | Lyden et al. |

FOREIGN PATENT DOCUMENTS

| EP | 0670170 A1 | 9/1995 |
| EP | 0718010 A1 | 6/1996 |
| JP | 4-24574 | 1/1992 |
| JP | 08-047543 | 2/1996 |

(Continued)

OTHER PUBLICATIONS

"U.S. Appl. No. 11/276,159, Final Office Action mailed Aug. 20, 2008", 5 pgs.

(Continued)

*Primary Examiner* — Rex Holmes
(74) *Attorney, Agent, or Firm* — Schwegman Lundberg & Woessner, P.A.

(57) ABSTRACT

An implantable medical device with an inductive switching regulator having an inductor with a ferromagnetic core is described. The device incorporates a core saturation detector for detecting saturation in the inductor core indicating the presence of a magnetic field such as produced by an MRI scan. The device is configured to alter its behavior when core saturation is detected such as by entering an MRI mode that may include cessation of therapy, fixed-rate bradycardia pacing, and/or disablement of tachyarrhythmia therapy.

20 Claims, 6 Drawing Sheets

FOREIGN PATENT DOCUMENTS

| | | |
|---|---|---|
| JP | 08-215323 | 8/1996 |
| JP | 200521688 A | 1/2005 |
| WO | WO-03063962 A1 | 8/2003 |
| WO | WO-2005/035048 A2 | 4/2005 |
| WO | WO-2006/081434 A1 | 8/2006 |
| WO | WO-2007/094976 A1 | 8/2007 |

OTHER PUBLICATIONS

"U.S. Appl. No. 11/276,159, Non-Final Office Action mailed Oct. 26, 2007", 6 pgs.

"U.S. Appl. No. 11/276,159, Notice of Allowance mailed Nov. 14, 2008", 4 pgs.

"U.S. Appl. No. 11/276,159, Response filed Feb. 26, 2008 to Non-Final Office Action mailed Oct. 26, 2007", 9 pgs.

"U.S. Appl. No. 11/276,159, Response filed Oct. 20, 2008 to Final Office Action mailed Aug. 20, 2008", 9 pgs.

"International Application Serial No. PCT/US2007/002848, International Search Report mailed Jun. 19, 2007", 5 pgs.

"International Application Serial No. PCT/US2007/002848, Written Opinion mailed Jun. 19, 2007", 8 pgs.

"European Application Serial No. 0774978.6, Office Action mailed Sep. 23, 2008", 2 pgs.

"European Application Serial No. 0774978.6, Response filed Oct. 22, 2008 to Office Action mailed Sep. 23, 2008", 16 pgs.

"European Application Serial No. 07749781.6, Office Action mailed Nov. 22, 2010", 4 pgs.

"Japanese Application Serial No. 2008-555259, Request for Examination and Voluntary Amendment filed Jan. 14, 2010", 8 pgs.

"European Application Serial No. 07749781.6, Response filed May 25, 2011 to Non Final Office Action mailed Nov. 22, 2010", 12 pgs.

"Japanese Application Serial No. 2008-555259, Office Action mailed Dec. 20, 2011", W/ English Translation, 8 pgs.

"Japanese Application Serial No. 2008-555259, Response filed Apr. 16, 2012 to Office Action mailed Dec. 20, 2011", (w/ English Translation of Amended Claims), 10 pgs.

* cited by examiner

MRI DETECTOR FOR IMPLANTABLE MEDICAL DEVICE

CROSS REFERENCE TO RELATED APPLICATION

This application is a continuation of U.S. application Ser. No. 11/276,159, filed Feb. 16, 2006, now issued as U.S. Pat. No. 7,509,167, which is hereby incorporated by reference in its entirety.

FIELD OF THE INVENTION

This disclosure pertains to implantable medical devices.

BACKGROUND

Cardiac rhythm management devices are implantable cardiac devices that provide electrical stimulation to selected chambers of the heart in order to treat disorders of cardiac rhythm. Examples of such devices include pacemakers and implantable cardioverter/defibrillators (ICDs). Cardiac devices rely upon their sensing capability in order to appropriately deliver stimulation to the heart. For example, pacemakers usually are programmed to deliver bradycardia pacing in a synchronous mode where paces are inhibited or triggered by sensed intrinsic cardiac activity. ICDs deliver shock therapy to the heart when the sensed cardiac activity indicates the presence of a tachyarrhythmia.

MRI (magnetic resonance imaging) scans pose risks to pacemaker and ICD patients due to possibility of interference with cardiac sensing which could cause inappropriate delivery of electrical stimulation. In order to mitigate these risks, devices are often reprogrammed to a non-sensing operating mode for the duration of the scan. However, device re-programming requires the intervention of both a knowledgeable professional and specialized equipment, neither of which may be conveniently available.

SUMMARY

Figure 1:
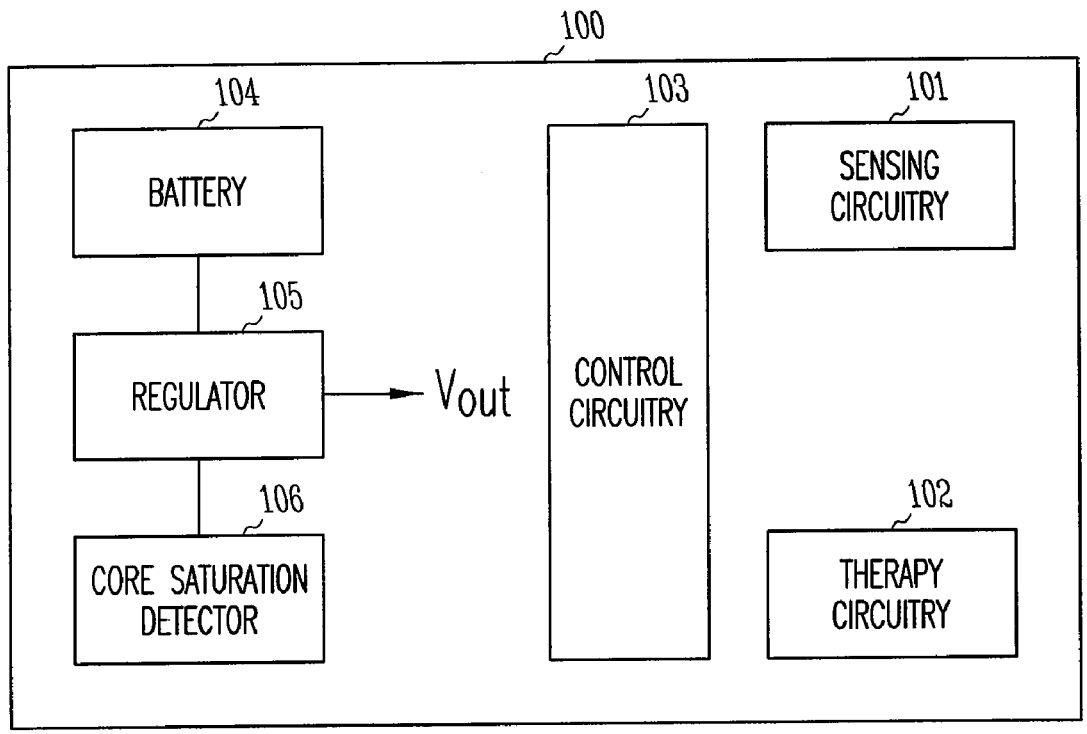
FIG. 1 shows the basic components of an implantable cardiac device.

As noted above, an MRI procedure also presents several risks to patients with implantable electronic devices such as pacemakers and defibrillators. For example, an implantable defibrillator may attempt to deliver inappropriate high-voltage therapy or may fail to deliver appropriate pacing therapy due to the large electromagnetic fields generated in an MRI interfering with the device's ability to properly sense cardiac activity. In an attempt to address these hazards, implantable cardiac rhythm management devices might offer an "MRI mode" that can be activated manually using an external programmer. This MRI mode would effectively force the device into a non-sensing, fixed-rate pacing mode so that consistent pacing therapy can be delivered. High-voltage tachyarrhythmia therapy might also be disabled in MRI mode to prevent inappropriate shocks from being administered by the device, with the patient being closely monitored during the MRI procedure.

While the activation of the aforementioned MRI mode might sufficiently mitigate the hazards presented to a pacemaker or defibrillator patient undergoing an MRI scan, this mitigation still requires the intervention of an external programmer and an electrophysiologist, cardiologist, or likewise skilled medical professional capable of temporarily re-programming the device into MRI mode. At the end of the MRI scan, this same specialized medical professional must restore the device to its previous mode of operation before the patient can be released. The burden of performing an MRI procedure on a pacemaker/defibrillator patient would be greatly reduced if these devices were equipped with a reliable means of detecting an MRI scan and automatically activating MRI mode when necessary. Described herein is a technique for detecting an MRI scan in an implantable medical device employing an inductive switching power supply by detecting saturation in the ferromagnetic core of the power supply's inductor. Core saturation occurs in the presence of large magnetic fields such as produced by an MRI scan.

DETAILED DESCRIPTION

One obvious indicator of an MRI scan is its extremely high magnetic field (0.5 to 5.0 Tesla). Pacemakers and ICDs commonly employ magnet detectors (e.g., reed switches, hall sensors) in order to detect the presence of a patient magnet used to signal the device to take some type of action (e.g., change its pacing mode before a programming session). These types of magnet detectors, however, are too sensitive to distinguish between an MRI scan and a patient magnet. An MRI detector that works by detecting a magnetic field needs to be insensitive enough to ignore a patient magnet or any other "day-to-day" environmental magnetic fields (less than 0.1 Tesla, for example).

Many pacemakers and ICDs devices use an inductive switching regulator type of power supply with a power inductor. Power inductors are constructed with a ferromagnetic core in order to increase inductance. The inductance of the inductor is effectively multiplied by the core permeability. Under strong magnetic fields, the core material can saturate, which dramatically lowers the inductance. By incorporating a core saturation detector into the device to detect a loss of inductance in the power inductor, the presence of a high magnetic field produced by an MRI scan can be detected with specificity.

FIG. 1 illustrates the basic components of an implantable cardiac device 100 which are relevant to the present discussion. Sensing circuitry 101 receives electrogram signals from internal electrodes which reflect the electrical activity of the heart. Therapy circuitry 102 includes pulse generation circuitry for generating pacing pulses and/or defibrillation shocks which are delivered to the heart via internal electrodes. Control circuitry 103 interprets the electrogram signals and controls the output of electrical stimulation to heart as needed in accordance with a normal operating mode. The power supply for the device includes a battery 104 and an inductive switching regulator 105. The inductive switching regulator 105 is a DC-DC converter which provides a stable and appropriate voltage level $V_{out}$ to the electronic circuitry of the device, including the sensing, therapy, and control circuitries. A core saturation detector 106 monitors one or more parameters during the operation of the switching regulator that vary as the inductance of the power inductor changes. When a strong magnetic field is present, such as produced by an MRI machine, the core of the power inductor saturates. The resulting decrease in inductance is then detected by the core saturation detector which produces a signal allowing the device to modify its operation accordingly. Upon detection of core saturation, the device may be configured to enter an MRI mode that may include non-sensing fixed-rate bradycardia pacing, disablement of tachyarrhythmia therapy, or any mode of operation deemed safe and desirable in a high electromagnetic field environment where sensing of cardiac activity is compromised. The device may then be further configured to automatically exit the MRI mode when the core saturation detector indicates that the high magnetic field is no longer present. The device thus automatically enters the MRI mode when an MRI scan begins and exits the MRI mode when the scan ends.

As will be described below, the core saturation detector may operate by measuring the time duration of one or more phases of the regulator's power conversion cycle, which depends upon the inductance of the power inductor in an inductive regulator operating in a synchronous current-limited mode, or by measuring the peak power inductor current in inductive regulators operating in other modes. In various embodiments, the control circuitry and core saturation detector may be implemented by discrete component circuitry and/or a microprocessor-based controller executing coded instructions.

Inductive Switching Regulators

Inductive switching regulators employ an inductor component with a ferromagnetic core in order to achieve a higher inductance value than could otherwise be realized with the same number of wire turns wound around an air core (or any other non-ferromagnetic material). The introduction of the ferromagnetic core material increases the inductance by a factor $\mu_m$ which represents the permeability of the core material. In the presence of a large external magnetic field, however, all of the magnetic domains in the ferromagnetic core material align with this magnetic field, causing the core to become "saturated". When the inductor core saturates, the effective inductance value of the inductor component drops dramatically (i.e., drops by a factor of $\mu_m$). To understand the effect this can have on the operation of an inductive switching supply, the basic operation of a typical synchronous inductive switching supply will now be described.

An inductive switching voltage regulator alternately stores and discharges energy in an inductor in a two-phase power conversion cycle, the power conversion phases designated as fill (or charge) and dump (or discharge) phases, respectively. Typically, inductive switching supplies operate in one of three basic configurations: buck (or step-down), boost (or step-up), or buck-boost (or inverting). In the examples of inductive switching regulators to be discussed, energy is alternately charged and discharged in an inductor. Other embodiments of an inductive switching regulator may employ a transformer as the inductive element, and the term inductor as used throughout this document should be taken to mean either a single-winding inductor or a transformer.

Figure 2:
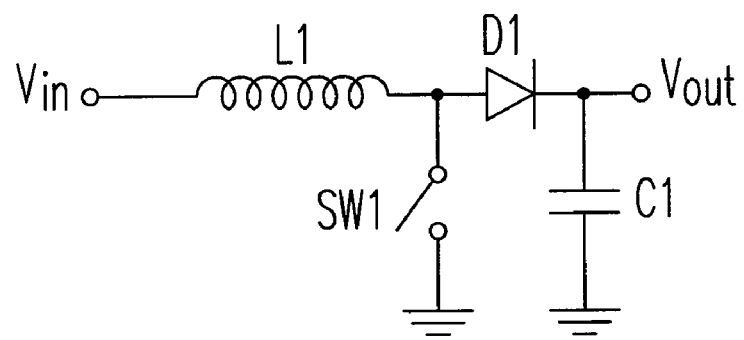
FIG. 2 illustrates a boost configuration inductive switching regulator.

A basic boost configuration is depicted in FIG. 2. During the fill phase, when the switch SW1 closes, the input voltage $V_{in}$ is impressed across the inductor L1, with the diode D1 preventing the capacitor C1 from discharging to ground. If the input voltage does not change appreciably, the current through the inductor L1 rises linearly with time at a rate that is proportional to the input voltage divided by the inductance of the inductor L1. The energy stored in the inductor during the fill phase is equal to one-half the inductance times the square of the peak current. The dump phase begins when the switch SW1 opens. The voltage across the inductor L1 then changes to whatever is required to maintain current flow, because the inductor current cannot change instantaneously. In order for current to continue flowing, the inductor voltage must change enough to forward-bias the diode D1. If the switch SW1 is repeatedly opened and closed to produce a sequence of power conversion cycles, the voltage $V_{out}$ across the capacitor C1 will rise with every cycle as the capacitor is charged by the inductor current.

Figure 3:
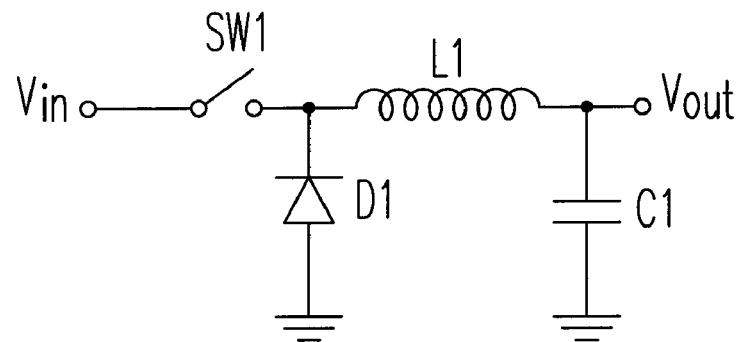
FIG. 3 illustrates a buck configuration inductive switching regulator.
Figure 4:
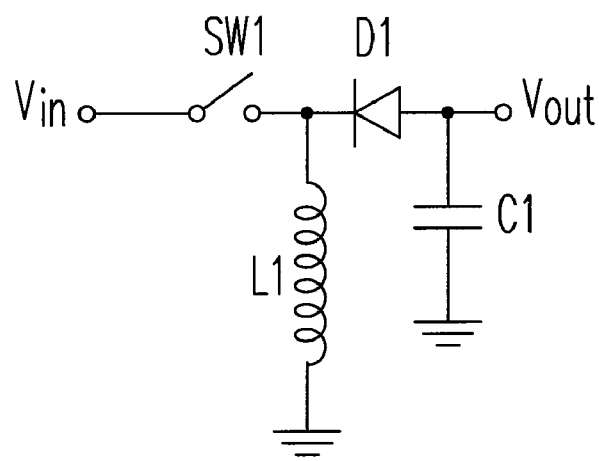
FIG. 4 illustrates a buck-boost configuration inductive switching regulator.

The same basic elements described in FIG. 2 can be rearranged to result in the buck configuration as shown in FIG. 3. In this configuration, when the switch SW1 closes during the fill phase, the voltage $V_{in}$ minus $V_{out}$ is impressed across the inductor L1, making the inductor current ramp up linearly and charge the output capacitor C1. The switch SW1 opens to start the dump phase, making the voltage across the inductor L1 change to maintain current flow, which then charges the output capacitor C1 through the diode D1. Interchanging the inductor and diode positions in the circuit yields the inverting or buck-boost configuration as depicted in FIG. 4. In this configuration, when the switch SW1 closes to start the fill phase, $V_{in}$ is impressed across the inductor, making the inductor current ramp up. When the switch opens to start the dump phase, the current flow is maintained by the voltage across the inductor. The inductor current during the dump phase then flows through the diode and charges the output capacitor to an output voltage $V_{out}$ with the opposite polarity to the input voltage $V_{in}$.

Figure 5:
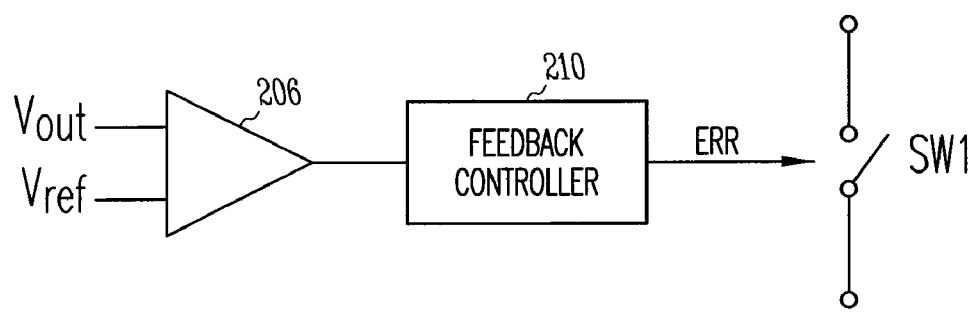
FIG. 5 illustrates a feedback control system for an inductive switching regulator.

A feedback control system may be used to regulate the output voltage $V_{out}$ in any of the embodiments of FIGS. 2-4 by operating the switch SW1 in accordance with an error signal. FIG. 5 shows a comparator 206 that compares the output voltage $V_{out}$ with a reference voltage $V_{ref}$ to generate an error signal ERR. The error signal then drives a feedback controller 210 that operates the switch SW1 in a manner tending to reduce the error signal. The feedback controller may be implemented in different ways, referred to herein as control modes. In a clocked frequency modulation control mode, the feedback controller gates an oscillator to operate the switch SW1 and generate power conversion cycles until the error signal is reduced. In a current-limited frequency modulation control mode (also referred to as a synchronous mode), the feedback controller similarly operates the switch SW1 to generate power conversion cycles until the error signal is reduced, but the durations of the fill and dump phases are made dependent upon the inductor current. The switch SW1 is operated so that the inductor current increases during the fill phase until a predetermined peak current value is reached and then decreases during the dump phase to zero or other predetermined value. In a pulse-width modulation control mode, the feedback controller operates the switch SW1 at a fixed frequency but varies the durations of the fill and dump phases to decrease the error signal (i.e., increases the duration of the fill phase to increase the output voltage and vice-versa).

Detection of Core Saturation

As mentioned previously, if an inductor's core material becomes saturated due to the application of a large external magnetic field (e.g., as would be the case during an MRI scan), the inductance value drops significantly. This will result in a much higher rate of change in inductor current during both power conversion phases. For a switching regulator operating in a current-limited frequency modulated control mode, this means that the fill and dump phases will happen much faster and the energy delivered to the load per power conversion cycle will be much lower as the energy storage of an inductor is given by: $0.5*L*I^2$. For a switching regulator operating in a clocked frequency modulation control mode or a pulse width modulation control mode, the peak inductor current during a power conversion cycle will increase.

Measurement of Power Conversion Phase Times in Current-Limited Control Mode

An inductive switching regulator operating in a current-limited control mode may be configured to generate three signals that are asserted to indicate the start and end of the power conversion phases for use by the core saturation detector. These signals are: FPS which marks the start of the fill phase, PKIC which indicates that the inductor current has reached its predetermined peak value and therefore signifies the end of the fill phase and the start of the dump phase, and ZIC which indicates that the inductor current is zero and therefore signifies the end of the dump phase. The core saturation detector 106 then measures the length of the fill and/or dump phase as the time intervals between FPS and PKIC and/or between PKIC and ZIC, respectively. A more detailed explanation and descriptions of different embodiments are set forth below.

Figure 6:
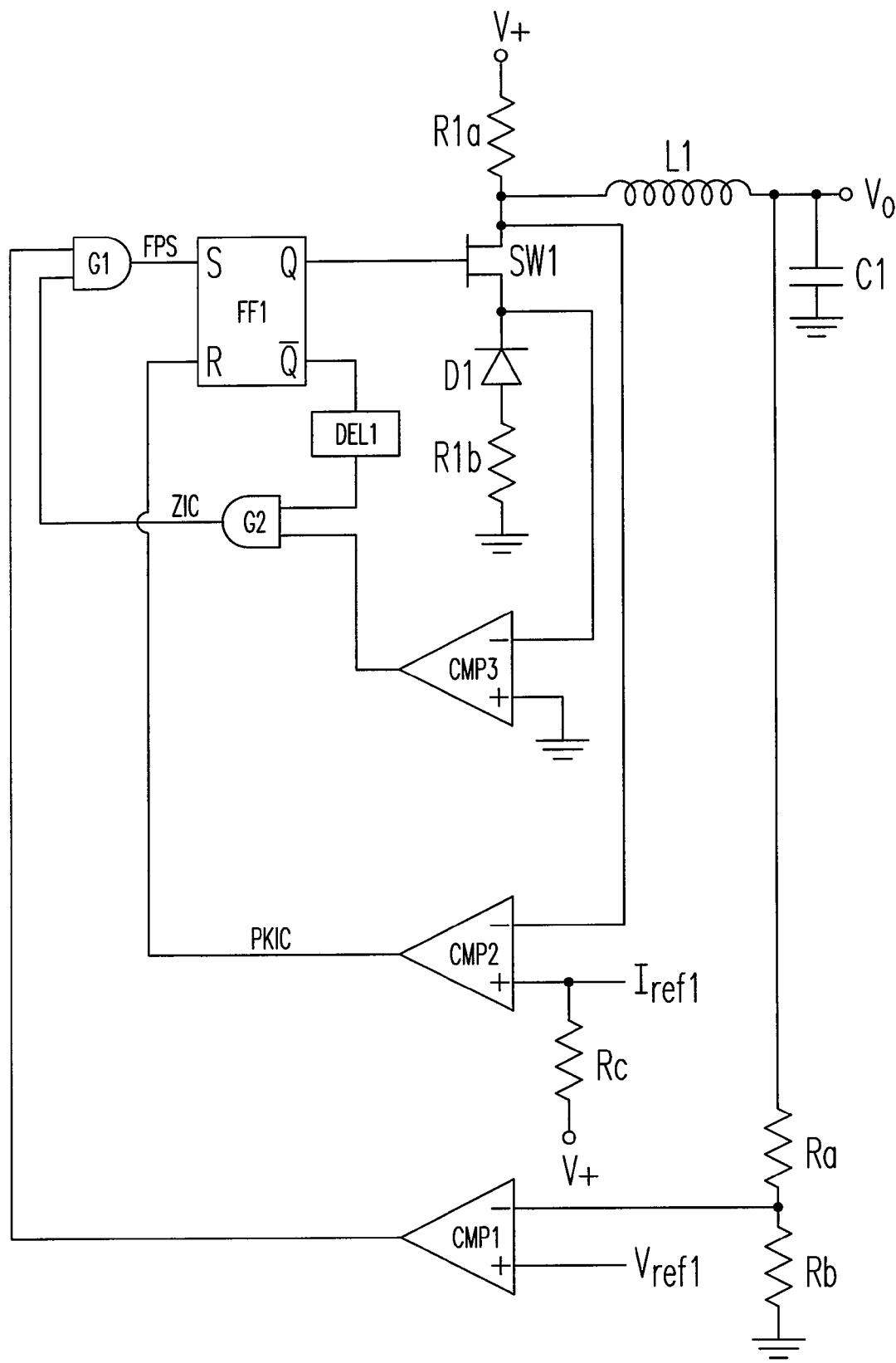
FIG. 6 illustrates a buck configuration inductive switching regulator operating in a current-limited control mode.
Figure 7:
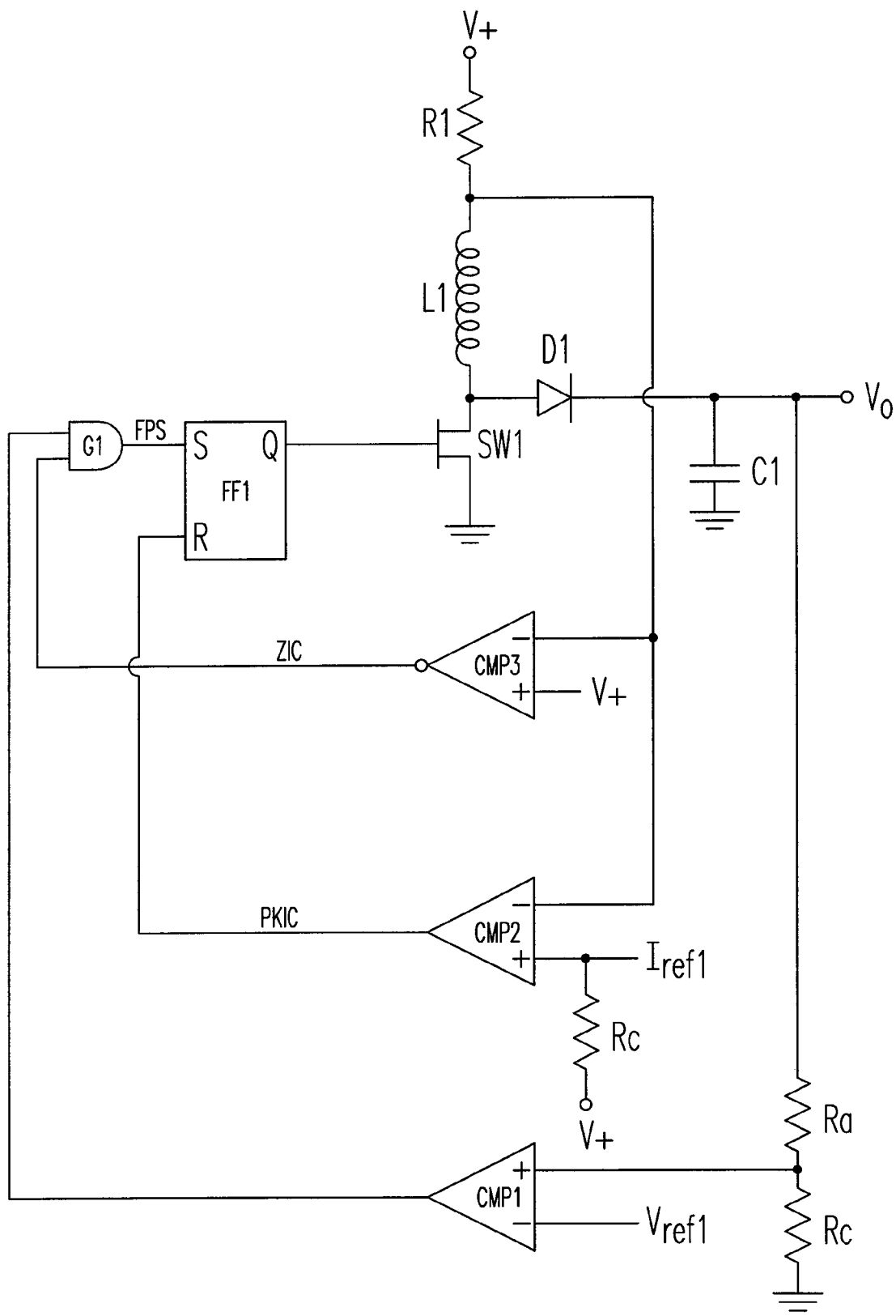
FIG. 7 illustrates a boost configuration inductive switching regulator operating in a current-limited control mode.
Figure 8:
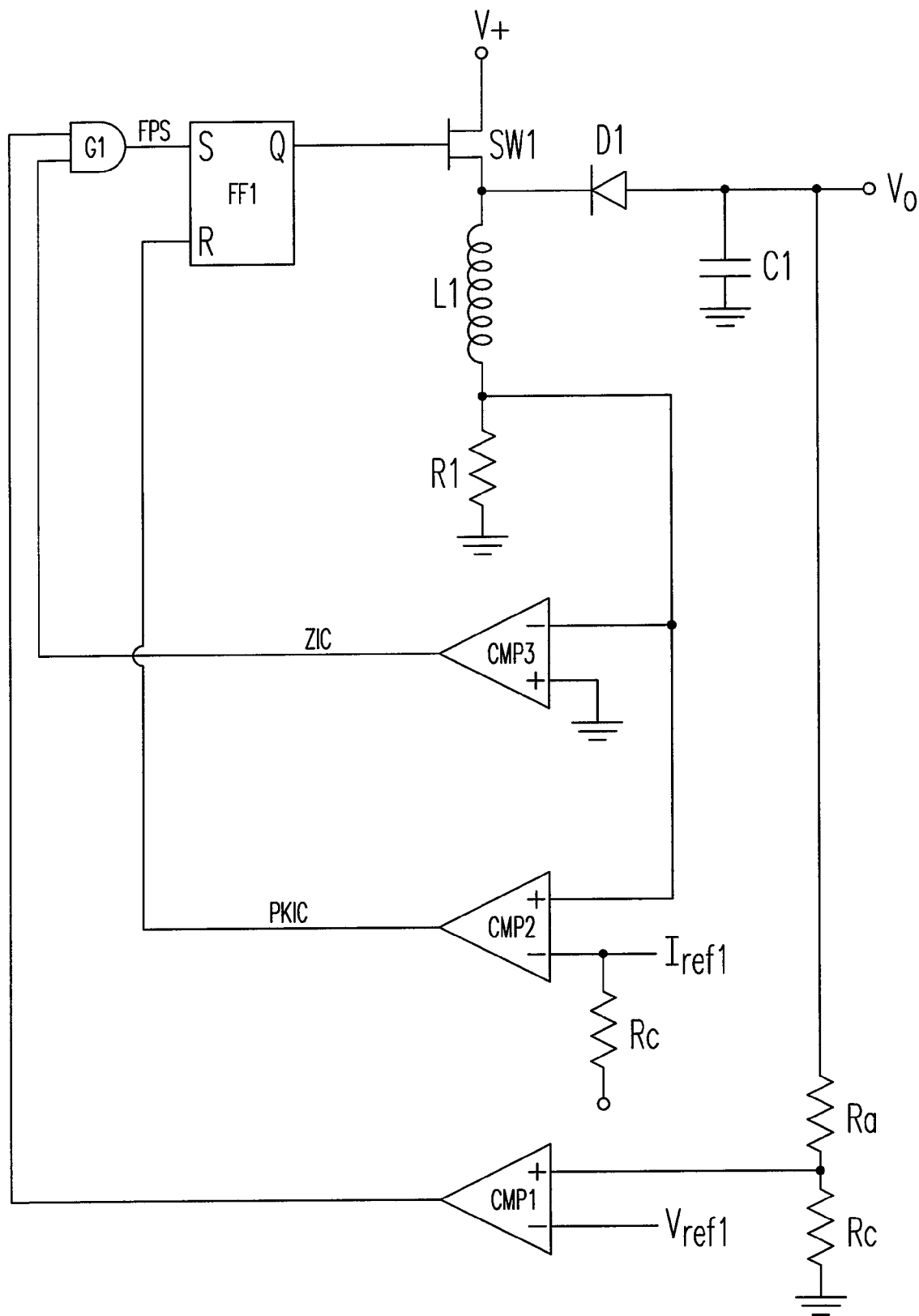
FIG. 8 illustrates a buck-boost configuration inductive switching regulator operating in a current-limited control mode.

FIGS. 6 through 8 are examples of inductive switching regulator circuits operating in a current-limited frequency control mode in buck, boost, and buck-boost configurations, respectively, and that include an inductor L1, switch SW1, capacitor C1, and diode D1. In a current-limited (or synchronous) control mode, the duration of the fill and dump phases during a power-conversion cycle is controlled via feedback from an inductor current monitor. During the fill phase, the inductor current starts at zero and ramps up towards a predetermined peak current value. Once this peak current value is reached, the fill phase is terminated and the dump phase begins. During the dump phase, the inductor current starts off at the peak current value and ramps back down towards zero. When the inductor current reaches zero, the dump phase is terminated, and either a new cycle can begin again or charging can stop as determined by a feedback loop which compares the output voltage of the regulator with a reference voltage.

FIG. 6 is an example of an inductive switching regulator circuit in a buck configuration. A MOS switch whose state is controlled by the output of flip-flop FF1 alternately switches the battery voltage $V_+$ across inductor L1 and capacitor C1, the capacitor voltage being the output voltage $V_o$ of the regulator. When switch SW1 closes, the fill phase begins and the inductor current increases linearly, assuming a constant voltage across the inductor L1. When switch SW1 opens, the fill phase ends and the dump phase begins. During the dump phase, the voltage across L1 reverses polarity so as to maintain the flow of inductor current. The current through inductor L1 then flows through diode D1 in a linearly decreasing fashion, assuming a constant voltage across the inductor. The durations of the fill and dump phases are controlled by circuitry which monitors the inductor current. A portion of the output voltage $V_o$ is fed back via a voltage divider made up of resistors $R_a$ and $R_b$ to a comparator CMP1 where it is compared with a reference voltage $V_{ref1}$. If the output voltage is low, so that the output of CMP1 is asserted, a power conversion cycle begins. The inductor current is measured with current sense resistors R1a and R1b whose voltages are fed to comparators CMP2 and CMP3, respectively. During the dump phase, the inverted output of comparator CMP3 is asserted when the inductor current is zero, as indicated by the assertion of AND gate G2 to give the signal ZIC. Comparator CMP3 must have a small negative input offset voltage to ensure that the ZIC signal is always asserted whenever the inductor current is zero. Also, delay element DEL1 and AND gate G2 ensure that the output of comparator CMP3 is only allowed to determine the state of signal ZIC when the output of comparator CMP3 is valid. These circuit elements thus form a zero current detector. The rising edge of signal ZIC signifies that the previous dump cycle has ended as the inductor current has decreased to zero. The outputs of gate G2 and comparator CMP1 are ANDed together by gate G1 to result in signal FPS which when asserted begins the fill phase by setting flip-flop FF1, the output of which then closes switch SW1. The fill phase continues until the inductor current, which flows through sense resistor R1a during the fill phase, reaches its predetermined peak value. The voltage across resistor R1a is compared with a voltage derived from a reference current $I_{ref1}$ by comparator CMP2. The reference current $I_{ref1}$ is dropped across a resistor Rc with the values of the reference current and resistor chosen such that the output PKIC of comparator CMP2 is asserted when the inductor current reaches its predetermined peak value. These circuit elements thus form a peak current detector. The assertion of PKIC resets the flip-flop FF1 and signifies the end of the fill phase and the beginning of the dump phase. In FIGS. 7 and 8, the same components are rearranged to result in inductive switching regulators in boost and buck-boost configurations, respectively, the operations of which are similar to that of the buck configuration just described. The start of the fill phase, end of the fill phase, and end of the dump phase are again indicated by assertions of the FPS, PKIC, and ZIC signals, respectively. (Note that only one current sense resistor R1 and one AND gate G1 are used to implement the inductor current monitor for the circuits of FIGS. 7 and 8.)

In one exemplary embodiment, the length of the fill phase is measured and compared to a threshold value to determine if core saturation exists. For example, in a boost or inverting configuration, the battery or input voltage is impressed across the inductor during the fill phase. If the battery voltage does not change significantly during the fill phase of an individual charging cycle, then the inductor current exhibits a fairly constant rate of change (dI/dt) during that phase. That is, the inductor current changes linearly if the voltage across the inductor is constant. The duration of the fill phase $t_{fill}$ is then linearly related to the inductance L of the inductor L1 and is given by:

$$t_{fill}=(I_{peak}*L)/V_+$$

where $I_{peak}$ is the predetermined peak value of the inductor current and $V_+$ is the battery voltage. When the inductor core saturates, L is reduced by a factor of $\mu_m$ (the permeability of the core material). Suppose we have the following parameters:

L=300 µH
$I_{peak}$=50 mA
$V_+$=3 V
$\mu_m$=50

During normal operation:

$$t_{fill}=(I_{peak}*L)/V_+=(50\text{ mA})(300\text{ µH})/(3\text{ V})=5\text{ µs}$$

When the inductor core saturates:

$$t_{fill}=(I_{peak}*L)/V_+=(50\text{ mA})(6\text{ µH})/(3\text{ V})=100\text{ ns}$$

An exemplary detection threshold could declare core saturation whenever $t_{fill}$<1 μs.

In another exemplary embodiment, the length of the dump phase is measured and compared to a threshold value to determine if core saturation exists. For example, in a buck configuration, the output voltage is impressed across the inductor during the dump phase (neglecting the forward bias voltage of the diode D1). The duration of the dump phase $t_{dump}$ is then linearly related to the inductance L of the inductor L1 and is given by:

$$t_{dump}=(I_{peak}*L)/V_{out}$$

where $I_{peak}$ is the predetermined peak value of the inductor current and $V_{output}$ is the battery voltage. Again, when the inductor core saturates, L is reduced by a factor of $\mu_m$ (the permeability of the core material). Suppose we have the following parameters:

L=300 μH
$I_{peak}$=25 mA
$V_{output}$=3 V
$\mu_m$=50

During normal operation:

$$t_{dump}=(I_{peak}*L)/V_{output}=(25 \text{ mA})(300 \text{ μH})/(3 \text{ V})=2.5 \text{ μs}$$

When the inductor core saturates:

$$t_{dump}=(I_{peak}*L)/V_{output}=(25 \text{ mA})(6 \text{ μH})/(3 \text{ V})=50 \text{ ns}$$

An exemplary detection threshold could declare core saturation whenever $t_{dump}$<0.5 μs.

In a current-limited switching regulator in either a buck, boost, or inverting configuration, the core saturation detector 106 may measure the length of the fill phase $t_{fill}$ as the time interval between the assertions of the FPS signal and the PKIC signal, the dump phase $t_{dump}$ as the time interval between the assertions of PKIC and ZIC, or the total power conversion cycle time as the time interval between the assertions of FPS and ZIC. The core saturation detector then compares the measured time interval to a specified threshold value to determine if core saturation exists, where the comparison function may be implemented in the programming of the controller and/or as discrete components. In an exemplary embodiment, the core saturation detector includes a delay element to establish the minimum allowable time interval between starting and stopping events. In an alternate embodiment, the core saturation detector includes a counter that is started and reset by one phase signal and stopped by another phase signal (e.g., started and reset by FPS and stopped by PKIC in order to measure the fill phase duration). The counter's value is then compared with a specified threshold value. If the counter's value is above the threshold, a bit is set that is readable by the controller to indicate that core saturation is detected.

Figure 9:
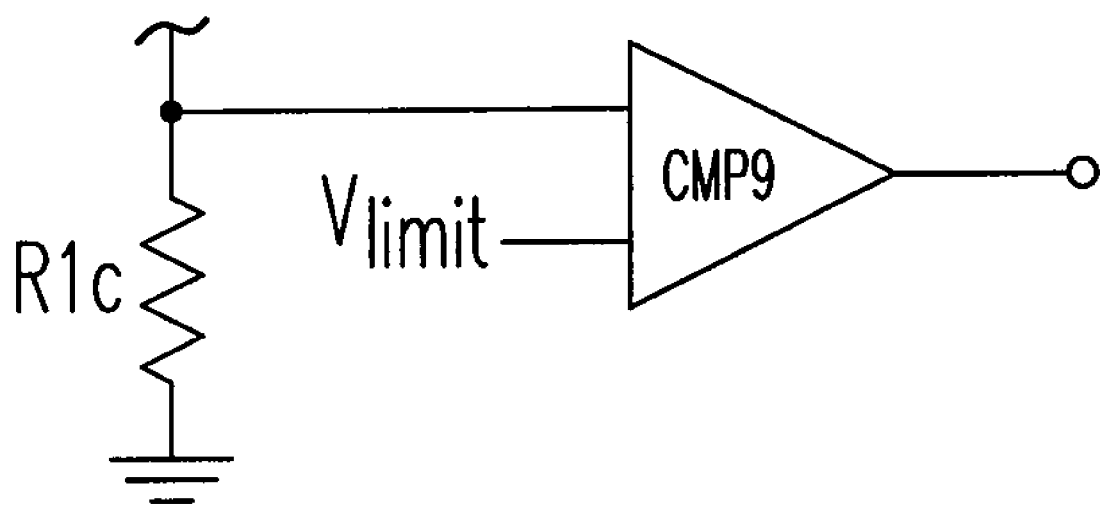
FIG. 9 illustrates components for measuring inductor current in order to detect core saturation.

Measurement of Peak Inductor Current in Clocked Frequency Modulation and Pulse-Width Modulation Control Modes In an inductive switching regulator operating in a clocked frequency modulation or a pulse-width modulation control mode, the peak inductor current during a power conversion cycle will increase drastically if the inductor core saturates. In order to detect core saturation, the current through the inductor in any of the buck, boost, or inverting configurations can be measured and compared with a specified threshold value. The specified threshold is set to value well above any inductor current value expected to occur under normal operating conditions. Inductor current may be measured using similar components to those used to measure inductor current for the current-limited control modes illustrated in FIGS. 6-8. FIG. 9 shows an embodiment in which the voltage across a current sense resistor R1c is fed to a comparator CMP9. If the voltage across the resistor R1c exceeds a limit value $V_{limit}$ corresponding to an inductor current above the specified threshold value, core saturation is detected. The output of the comparator CMP9 may be used to set a bit readable by the controller.

Uses of Core Saturation Detection

As described above, upon detection core saturation indicating the presence of an MRI magnetic field, an implantable cardiac device may be programmed to enter a noise reversion mode (a.k.a., an MRI mode), which may include cessation of therapy, asynchronous pacing and/or inhibition of tachyarrhythmia therapy such as ATP and defibrillation shocks. Other types of implantable medical devices that are adversely affected by a large magnetic field may similarly enter a noise reversion mode of some kind upon detection of core saturation. Also, if the reduction in inductance resulting from core saturation is great enough, a switching regulator may fail to deliver adequate performance unless steps are taken to compensate for the temporary loss in inductance. To deal with this situation, the device could be programmed to alter the operation of switching regulator (e.g., increase inductor peak current in a current-limited control mode or increase pulse width in a clocked frequency modulation control mode) and/or enter a power saving mode in order to reduce the load on the regulator. After entering an MRI mode that alters device behavior in any of the ways just discussed, the device may be further configured to return to its normal operating mode when core saturation is no longer detected.

Although the invention has been described in conjunction with the foregoing specific embodiments, many alternatives, variations, and modifications will be apparent to those of ordinary skill in the art. Such alternatives, variations, and modifications are intended to fall within the scope of the following appended claims.

What is claimed is:

1. A device, comprising: an implantable medical device, further comprising:
   an inductive switching regulator having an inductor with a ferromagnetic core;
   wherein the inductive switching regulator alternately stores and discharges energy in the inductor in a power conversion cycle;
   a core saturation detector for detecting saturation in the inductor core of the inductive switching regulator indicating the presence of a magnetic field by monitoring the power conversion cycle; and,
   circuitry for producing a core saturation signal when core saturation is detected.

2. The device of claim 1 further comprising:
   sensing circuitry for receiving electrogram signals that reflect the electrical activity of the heart;
   therapy circuitry for delivering electrical stimulation to the heart;
   control circuitry for controlling the delivery of electrical stimulation to the heart in a normal operating mode; and,
   circuitry for causing the device to enter a non-sensing MRI mode upon detection of core saturation.

3. The device of claim 2 wherein the MRI mode includes cessation of the delivery of electrical stimulation to the heart.

4. The device of claim 2 wherein the MRI mode includes fixed-rate bradycardia pacing.

5. The device of claim 2 wherein the MRI mode includes disablement of delivery of tachyarrhythmia therapy by the therapy circuitry.

6. The device of claim 1 wherein the inductive switching regulator alternately stores and discharges energy in an inductor in a two-phase power conversion cycle, the power conversion phases designated as fill and dump phases, respectively, such that the inductor current increases until a predetermined peak current value is reached during the fill phase and decreases to zero or other predetermined value during the dump phase, and further comprising:
- circuitry for measuring the duration of the fill phase during a power conversion cycle; and,
- wherein the core saturation detector detects core saturation if the duration of the fill phase exceeds a specified threshold value.

7. The device of claim 1 wherein the inductive switching regulator alternately stores and discharges energy in an inductor in a two-phase power conversion cycle, the power conversion phases designated as fill and dump phases, respectively, such that the inductor current increases until a predetermined peak current value is reached during the fill phase and decreases to zero or other predetermined value during the dump phase, and further comprising:
- circuitry for measuring the duration of the dump phase during a power conversion cycle; and,
- wherein the core saturation detector detects core saturation if the duration of the dump phase exceeds a specified threshold value.

8. The device of claim 1 wherein the inductive switching regulator alternately stores and discharges energy in an inductor in a two-phase power conversion cycle, the power conversion phases designated as fill and dump phases, respectively, such that the inductor current increases until a predetermined peak current value is reached during the fill phase and decreases to zero or other predetermined value during the dump phase, and further comprising:
- circuitry for measuring the duration of a power conversion cycle; and,
- wherein the core saturation detector detects core saturation if the duration of the power conversion cycle exceeds a specified threshold value.

9. The device of claim 1 wherein the inductive switching regulator operates in a clocked frequency modulation or pulse width modulation control mode, and further comprising:
- circuitry for measuring the peak inductor current during a power conversion cycle; and,
- wherein the core saturation detector detects core saturation if the peak inductor current exceeds a specified threshold value.

10. The device of claim 2 wherein the device is configured to revert to the normal operating mode when core saturation is no longer detected.

11. A method, comprising:
- operating an implantable medical device incorporating an inductive switching regulator having an inductor with a ferromagnetic core;
- operating the inductive switching regulator to alternately store and discharge energy in the inductor in a power conversion cycle;
- detecting saturation in the inductor core of the inductive switching regulator indicating the presence of a magnetic field by monitoring the power conversion cycle; and,
- producing a core saturation signal when core saturation is detected.

12. The method of claim 11 further comprising:
- receiving electrogram signals that reflect the electrical activity of the heart;
- delivering therapy in the form of electrical stimulation to the heart in accordance with a normal operating mode; and
- entering a non-sensing MRI mode upon detection of core saturation.

13. The method of claim 12 wherein the MRI mode includes cessation of the delivery of electrical stimulation to the heart.

14. The method of claim 12 wherein the MRI mode includes fixed-rate bradycardia pacing.

15. The method of claim 12 wherein the MRI mode includes disablement of delivery of tachyarrhythmia therapy.

16. The method of claim 11 wherein the inductive switching regulator alternately stores and discharges energy in an inductor in a two-phase power conversion cycle, the power conversion phases designated as fill and dump phases, respectively, such that the inductor current increases until a predetermined peak current value is reached during the fill phase and decreases to zero or other predetermined value during the dump phase, and further comprising:
- measuring the duration of the fill phase during a power conversion cycle; and,
- detecting core saturation if the duration of the fill phase exceeds a specified threshold value.

17. The method of claim 11 wherein the inductive switching regulator alternately stores and discharges energy in an inductor in a two-phase power conversion cycle, the power conversion phases designated as fill and dump phases, respectively, such that the inductor current increases until a predetermined peak current value is reached during the fill phase and decreases to zero or other predetermined value during the dump phase, and further comprising:
- measuring the duration of the dump phase during a power conversion cycle; and,
- detecting core saturation if the duration of the dump phase exceeds a specified threshold value.

18. The method of claim 11 wherein the inductive switching regulator alternately stores and discharges energy in an inductor in a two-phase power conversion cycle, the power conversion phases designated as fill and dump phases, respectively, such that the inductor current increases until a predetermined peak current value is reached during the fill phase and decreases to zero or other predetermined value during the dump phase, and further comprising:
- measuring the duration of a power conversion cycle; and,
- detecting core saturation if the duration of the power conversion cycle exceeds a specified threshold value.

19. The method of claim 11 wherein the inductive switching regulator operates in a clocked frequency modulation or pulse width modulation control mode, and further comprising:
- measuring the peak inductor current during a power conversion cycle; and,
- detecting core saturation if the peak inductor current exceeds a specified threshold value.

20. The method of claim 12 further comprising reverting to the normal operating mode when core saturation is no longer detected.

* * * * *